United States Patent
Eller et al.

[11] Patent Number: 5,773,660
[45] Date of Patent: Jun. 30, 1998

[54] PREPARATION OF AMINES FROM OLEFINS OVER HEXAGONAL FAUJASITES

[75] Inventors: Karsten Eller, Ludwigshafen; Rudolf Kummer, Frankenthal; Eugen Gehrer, Ludwigshafen, all of Germany

[73] Assignee: BASF Aktiengesellschaft, Ludwigshafen, Germany

[21] Appl. No.: 784,548

[22] Filed: Jan. 21, 1997

[30] Foreign Application Priority Data

Jan. 26, 1996 [DE] Germany .................. 196 02 709.8

[51] Int. Cl.[6] ................................................ C07C 209/02
[52] U.S. Cl. .................. 564/485; 564/408; 564/445; 540/450; 546/184; 548/564; 548/579
[58] Field of Search ................................. 564/408, 445, 564/485

[56] References Cited

U.S. PATENT DOCUMENTS

| | | | |
|---|---|---|---|
| 4,536,602 | 8/1985 | Deeba | 564/485 |
| 5,648,546 | 7/1997 | Bergfeld | 564/485 |

FOREIGN PATENT DOCUMENTS

| | | |
|---|---|---|
| 2092964 | 3/1993 | Canada . |
| 039 918 | 11/1981 | European Pat. Off. . |
| 101 921 | 3/1984 | European Pat. Off. . |
| 132 736 | 2/1985 | European Pat. Off. . |
| 133 938 | 3/1985 | European Pat. Off. . |
| 305 564 | 3/1989 | European Pat. Off. . |
| 431 451 | 6/1991 | European Pat. Off. . |
| 587 424 | 3/1994 | European Pat. Off. . |
| 42 06 992 | 3/1992 | Germany . |

OTHER PUBLICATIONS

Brunet et al., Journal of Molecular Catalysis, vol. 49, pp. 235–259 (1989).

Primary Examiner—Richard L. Raymond
Attorney, Agent, or Firm—Keil & Weinkauf

[57] ABSTRACT

A process for preparing amines of the formula I

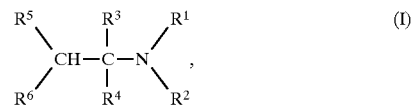

where $R^1, R^2, R^3, R^4, R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ is $C_{21}$–$C_{200}$-alkyl or $C_{21}$–$C_{200}$-alkenyl or together they are a $C_2$–$C_{12}$-alkylene dichain, by reacting olefins of the formula II

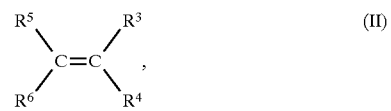

where $R^3$, $R^4$, $R^5$ and $R^6$ are each as defined above, with ammonia or primary or secondary amines of the formula III

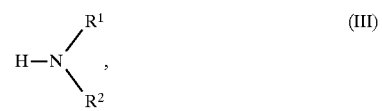

where $R^1$ and $R^2$ are each as defined above, at temperatures from 200° to 350° C. and pressures from 100 to 300 bar in the presence of a heterogeneous catalyst using a heterogeneous catalyst comprising hexagonal faujasite.

12 Claims, No Drawings

PREPARATION OF AMINES FROM OLEFINS OVER HEXAGONAL FAUJASITES

The present invention relates to a process for preparing amines by reacting ammonia or primary or secondary amines with olefins at elevated temperatures and pressures in the presence of zeolites of the type EMT.

Methods for aminating olefins are reviewed in Functionalisation of Alkenes: Catalytic Amination of Monoolefins, J. J. Brunet et al. J. Mol. Catal., 49 (1989), 235–259.

There are basically two mechanisms of catalysis. The olefin is coordinated via a metal complex. This activated species can be attacked by the nucleophilic amine to form a more highly aminated product. The amine can be chemisorbed on acid centers or on metal centers (via metal amides) and reacted with the olefin in this activated state.

Zeolites are suitable catalysts. They have a large number of catalytically active centers coupled with a large surface area. The zeolites which have been described differ in type and in the aftertreatment (eg. thermal treatment, dealumination, acid treatment, metal ion exchange, etc.). Examples may be found in U.S. Pat. No. 4,536,602, EP-A-101 921 or DE-A-42 06 992.

EP-A-133 938, EP-A-431 451 and EP-A-132 736 disclose processes wherein borosilicate, gallium silicate, aluminosilicate and iron silicate zeolites are used for preparing amines from olefins and mention the possibility of doping these zeolites with alkali, alkaline earth and transition metals.

CA-A-2 092 964 discloses a process for preparing amines from olefins using BETA zeolites, defined as crystalline aluminosilicates of a certain composition with a pore size of greater than 5 Å. Preference is given to using metal- or halogen-modified BETA zeolites.

EP-A-39 918 discloses a process for preparing amines from olefins over various faujasites of the zeolite Y or X type. The conversions obtained, not more than 6.5% in the case of isobutene, for example, are very low, however.

EP-A-305 564 utilizes faujasites of the type Y, partly in dealuminated form, for amination reactions. Again not more than 7.8% conversion is achieved with isobutene.

EP-A-587 424 achieves higher conversions (max 17.1%) with dealuminated Y zeolites, but the space velocities used are small and the space-time yields are too low for industrial applications.

All processes for synthesizing amines from olefins over these catalysts have a low amine yield or a low space-time yield or lead to rapid deactivation of the catalysts.

It is an object of the present invention to remedy these disadvantages.

We have found that, surprisingly, this object is achieved on using hexagonal faujasites (EMT) instead of the cubic faujasites (FAU) previously used.

The present invention accordingly provides a novel and improved process for preparing amines of the general formula I

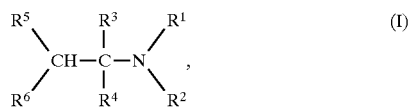

where
$R^1, R^2, R^3, R^4, R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ is $C_{21}$–$C_{200}$-alkyl or $C_{21}$–$C_{200}$-alkenyl or together they are a $C_2$–$C_{12}$-alkylene dichain, by reacting olefins of the general formula II

where $R^3$, $R^4$, $R^5$ and $R^6$ are each as defined above, with ammonia or primary or secondary amines of the general formula III

where $R^1$ and $R^2$ are each as defined above, at temperatures from 200° to 350° C. and pressures from 100 to 300 bar in the presence of a heterogeneous catalyst, which comprises using a heterogeneous catalyst comprising hexagonal faujasite.

The process of the present invention can be carried out as follows:

The olefin II and ammonia or the primary or secondary amine III can be reacted at temperatures from 200° to 350° C., preferably from 220° to 330° C., particularly preferably from 230° to 320° C., and pressures from 100 to 300 bar, preferably from 120 to 300 bar, particularly preferably from 140 to 290 bar, in the presence of hexagonal faujasites as catalyst, for example in a pressure reactor, and preferably the amine obtained is separated off and the unconverted feed materials are recycled.

The present process is notable for a very good yield combined with high selectivity and a high space-time yield. In addition, the deactivation of the catalyst is suppressed.

The process of the present invention is notable for the fact that even a small excess of ammonia or amine will produce a high selectivity in respect of the desired reaction product and will inhibit the dimerization and/or oligomerization of the olefin used.

In one embodiment of this process, ammonia and/or amines III are fed together with the olefin II in a mixture in a molar ratio of from 1:1 to 5:1 into a fixed-bed reactor and reacted therein at a pressure of from 100 to 300 bar and a temperature of from 200° to 350° C. in the gas phase or in the supercritical state.

The desired product can be obtained from the reaction effluent with the aid of known methods, for example distillation or extraction, and if necessary brought to the desired purity by means of further separating operations. The unconverted feed materials are generally preferably recycled into the reactor.

It is possible to use monounsaturated or polyunsaturated olefins II, in particular those having from 2 to 10 carbon atoms, or mixtures thereof and polyolefins as starting materials. Owing to the less pronounced tendency to polymerize, monoolefins are more suitable than di- and polyolefins, but the latter can be reacted just as selectively by means of higher ammonia or amine excesses. The position of the equilibrium and hence the conversion to the desired amine is very highly dependent on the reaction pressure used. High pressure favors the addition product, but the range of up to 300 bar will generally represent the optimum for technical and commercial reasons. The selectivity of the reaction is influenced not only by variables such as ammonia/amine excess and catalyst but also to a high degree by the temperature. It is true that the reaction rate of the addition reaction increases strongly with increasing temperature, but competing cracking and recombination reactions of the olefin are promoted at the same time. In addition, a temperature increase is not advantageous from a thermodynamic aspect. The position of the temperature optimum as regards conversion and selectivity is dependent on the constitution of the olefin, of the amine used and of the catalyst and is usually within the range from 200° to 350° C.

Suitable catalysts for the amination of olefins are hexagonal faujasites (EMT) or their mixed crystals with cubic faujasite (EMT-FAU). Such materials are known for example from zeolites 11 (1991), 98, and are also known as EMC-2 (EMT); another designation is Breck Structure Six (BSS). EMT-FAU intermediates are known as CSZ-1 from U.S. Pat. No. 4,309,313, CSZ-3 from U.S. Pat. No. 4,333, 859, ECR-4 from U.S. Pat. No. 4,714,601, ECR-17 from EP-A-259 526, ECR-30 from EP-A-315 461, ECR-32, LZ-267 from U.S. Pat. No. 4,503,023, ZSM-3 from U.S. Pat. No. 3,415,736 or ZSM-20 from U.S. Pat. No. 3,972,983.

The hexagonal faujasites of the present invention can be molded as such or else using a binder in a ratio of from 98:2 to 40:60% by weight into extrudates or tablets. Suitable binders include various aluminas, preferably boehmite, amorphous aluminosilicates having an $SiO_2/Al_2O_3$ ratio of from 25:75 to 95:5, silica, preferably finely divided $SiO_2$, mixtures of finely divided $SiO_2$ and finely divided $Al_2O_3$, finely divided $TiO_2$, and also clays. After molding, the extrudates or tablets are advantageously dried at 110° C. for 16 h and calcined at from 200° to 500° C. for from 2 to 16 h and the calcination can also take place directly (in situ) in the amination reactor.

To enhance the selectivity, the on-stream time and the number of possible regenerations, various modifications can be effected to the hexagonal faujasites of the present invention.

One way of modifying the catalysts comprises ion-exchanging or doping the molded or unmolded hexagonal faujasites with alkali metals such as Na and K, alkaline earth metals such as Ca and Mg, earth metals such as Tl, transition metals such as, for example, Ti, Zr, Mn, Fe, Mo, Cu, Zn and Cr, noble metals and/or rare earth metals such as, for example, La, Ce and Y.

An advantageous embodiment comprises presenting the molded hexagonal faujasites of the present invention in a flow tube and passing for example a halide, an acetate, an oxalate, a citrate or a nitrate of the above-described metals thereover in dissolved form at from 20° to 100° C. Such an ion exchange can be carried out for example on the hydrogen, ammonium or alkali metal form of the hexagonal faujasites of the present invention.

A further way of applying metal to the hexagonal faujasites of the present invention comprises impregnating the material for example with a halide, a nitrate, an acetate, an oxalate, a citrate or an oxide of the above-described metals in aqueous or alcoholic solution.

Both an ion exchange and an impregnation may be followed by drying, alternatively by a further calcination. In the case of metal-doped hexagonal faujasites, an aftertreatment with hydrogen and/or with water vapor can be advantageous.

A further way of achieving modification comprises subjecting the hexagonal faujasites of the present invention—molded or unmolded—to a treatment with acids, such as hydrochloric acid (HCl), hydrofluoric acid (HF), sulfuric acid ($H_2SO_4$), oxalic acid ($HO_2C-CO_2H$), phosphoric acid ($H_3PO_4$) or mixtures thereof.

A particular embodiment comprises refluxing the hexagonal faujasites of the present invention for from 1 to 100 hours with one of the aforementioned acids at from 0.001N to 2N, preferably from 0.05 to 0.5N, prior to molding. Collection by filtration and washing is generally followed by drying at from 100° to 160° C. and calcination at from 200° to 600° C. A further particular embodiment comprises an acid treatment of the hexagonal faujasites of the present invention after their molding with binder. Here the zeolite of the present invention is generally treated with an acid from 3 to 25% in strength, in particular from 12 to 20% in strength, at from 60° to 80° C. for from 1 to 3 hours, then washed, dried at from 100° to 160° C. and calcined at from 200° to 600° C. Here, too, it is again possible for the calcination to be carried out directly in the amination reactor.

Another way of achieving modification is by exchange with ammonium salts, for example with $NH_4Cl$, or with mono-, di- or polyamines. Here the binder-molded zeolite is generally exchanged at from 60° to 80° C. with a from 10 to 25% in strength, preferably 20% in strength, $NH_4Cl$ solution in a continuous manner for 2 h in a zeolite/ammonium chloride solution of 1:15 by weight and thereafter dried at from 100° to 120° C.

A further modification which can be carried out on the hexagonal faujasites of the present invention is a dealumination wherein some of the aluminum atoms are replaced by silicon or removed by a hydrothermal treatment, for example. A hydrothermal dealumination is advantageously followed by an extraction with acids or complexing agents in order that nonlattice aluminum formed may be removed. The replacement of aluminum by silicon can be effected for example with the aid of $(NH_4)_2SiF_6$ or $SiCl_4$. Examples of dealuminations of Y zeolites are found in Corma et al., Stud. Surf. Sci. Catal. 37 (1987), 495–503.

The catalysts can be used for the amination of olefins as extrudates having diameters from, for example, 1 to 4 mm or as tablets with diameters from, for example, 3 to 5 mm.

The catalyst, molded into extrudates for example, can be made to yield a fluidizable material from 0.1 to 0.8 mm in size by grinding and sieving.

The substituents $R^1$, $R^2$, $R^3$, $R^4$, $R^5$ and $R^6$ in the compounds I, II and III have the following meanings:
$R^1, R^2, R^3, R^4, R^5, R^6$ hydrogen, $C_1$–$C_{20}$-alkyl, preferably $C_1$–$C_{12}$-alkyl, particularly preferably $C_1$–$C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$–$C_{20}$-alkenyl, preferably $C_2$–$C_{12}$-alkenyl, particularly preferably $C_2$–$C_8$-alkenyl such as vinyl and allyl, $C_2$–$C_{20}$-alkynyl, preferably $C_2$–$C_8$-alkynyl, in particular $C_2H$ and propargyl, $C_3$–$C_{20}$-cycloalkyl, preferably $C_3$–$C_{12}$-cycloalkyl, particularly preferably $C_5$–$C_8$-cycloalkyl such as cyclopentyl, cyclohexyl, cycloheptyl and cyclooctyl, $C_4$–$C_{20}$-alkylcycloalkyl, preferably $C_4$–$C_{12}$-alkylcycloalkyl, particularly preferably $C_5$–$C_{10}$-alkylcycloalkyl, $C_4$–$C_{20}$-cycloalkylalkyl, preferably $C_4$–$C_{12}$-cycloalkylalkyl, particularly preferably $C_5$–$C_{10}$-cycloalkylalkyl, aryl such as phenyl, 1-naphthyl and 2-naphthyl, preferably phenyl, $C_7$–$C_{20}$-alkylaryl, preferably $C_7$–$C_{16}$-alkylaryl, preferably $C_7$–$C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-aralkyl, preferably $C_7$–$C_{16}$-aralkyl, preferably $C_7$–$C_{12}$-phenalkyl such as phenylmethyl, 1-phenylethyl, 2-phenylethyl, $R^1$ and $R^2$ together a saturated or unsaturated $C_3$–$C_9$-alkylene dichain, preferably —$(CH_2)_4$—, —$(CH_2)_5$—, —$(CH_2)_7$— and —CH=CH—CH=CH—, $R^3$ or $R^5$ $C_{21}$–$C_{200}$-alkyl, preferably $C_{40}$–$C_{200}$-alkyl, such as polybutyl, polyisobutyl, polypropyl, polyisopropyl und polyethyl, particularly preferably polybutyl and polyisobutyl, $C_{21}$–$C_{200}$-alkenyl, preferably $C_{40}$–$C_{200}$-alkenyl, particularly preferably $C_{70}$–$C_{170}$-alkenyl, $R^3$ and $R^5$ together a $C_2$–$C_{12}$-alkylene dichain, preferably a $C_3$–$C_8$-alkylene dichain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst Syntheses

Catalyst A: preparation of H-EMT 80 g of Na-EMT having an $SiO_2/Al_2O_3$ ratio of 7:1 were exchanged with 1200 g of 20% strength $NH_4Cl$ solution at 80° C. and then washed with 2 liters of water. After renewed $NH_4Cl$ exchange and washing the zeolite was dried at 120° C. for 2 hours and calcined at 500° C. for 5 hours. The entire process was repeated once more, and the sodium content of the zeolite before the last calcination was found to be 0.03% by weight.

65 g of H-EMT were compacted with 43 g of boehmite and 2.2 g of formic acid in a kneader and kneaded for 60 minutes with the addition of 68 ml of water. 2 mm extrudates were produced in an extruder under a molding pressure of 90 bar, dried at 120° C. for 4 hours and calcined at 500° C. for 16 hours.

Catalyst B: preparation of an HY zeolite (comparative example)

2160 g of NaY were admixed with 1440 g of boehmite and 72 g of formic acid, compacted in a kneader and kneaded for 60 minutes with the addition of 1850 ml of water. 2 mm extrudate were produced in an extruder under a molding pressure of 90 bar, dried at 110° C. for 16 hours and calcined at 500° C. for 16 hours. The ready-produced extrudates were treated similarly to catalyst A by ion-exchanging them four times with 20% strength $NH_4Cl$ solution at 80° C. and finally calcining them at 500° C. for 5 hours.

Catalyst C: preparation of an HX zeolite (comparative example)

13X extrudates from Union Carbide were treated similarly to catalyst A by ion-exchanging them four times with 20% strength $NH_4Cl$ solution at 80° C. After calcination, their sodium content was still 0.67%.

Catalyst D: preparation of a USY zeolite (comparative example)

180 g of a dealuminated Y zeolite from Grace (USY) were admixed with 120 g of boehmite and 6 g of formic acid, compacted in a kneader and kneaded for 45 min with the addition of 210 ml of water. 2 mm extrudates were produced in an extruder under a molding pressure of 80 bar, dried at 110° C. for 16 hours and calcined at 500° C. for 16 hours.

Catalyst E: preparation of an LaY zeolite (comparative example)

Na—Y extrudates from example B were exchanged twice with aqueous $La(NO_3)_3$ solution. According to analysis, the ready-produced catalyst contained 6.85% by weight of lanthanum and 1.5% by weight of sodium.

Catalyst F: preparation of a dealuminated EMT zeolite 20 g of catalyst A were installed in a rotary tube and dried at 80° C. for 2 hours with nitrogen (10 $l\cdot h^{-1}$). After cooling down to room temperature, the $N_2$ stream was admixed with $SiCl_4$ via a saturator and the temperature was raised to 460° C. in the course of 25 min, and held for 2 hours, and then the $SiCl_4$ supply was switched off and the catalyst was cooled down to room temperature under nitrogen. The removed catalyst was then calcined at 500° C. in air for 5 hours. The dealumination reduced the aluminum content from 22.3% by weight (catalyst A) to 18.8% by weight.

AMINATION EXAMPLES

The runs were carried out in a tubular reactor (6 mm internal diameter) under isothermal conditions at from 260° to 300° C. and a pressure of 280 bar using a mixture of isobutene and ammonia in a molar ratio of 1:1.5. The reaction products were analyzed by gas chromatography.

The results are summarized in Table 1 and show that the catalysts of the present invention provide higher yields than the prior art faujasite-based catalyst systems (H—X, H—Y) and that the yields are also above those of modified faujasites (dealuminated Y, La-exchanged Y).

TABLE 1 tert-butylamine ($NH_3$: $C_4H_8$ = 1.5)

| Catalyst | | | Tempera- | tert-Butylamine yield [wt %] | | | Weight per |
|---|---|---|---|---|---|---|---|
| No. | $Al_2O_3$ [wt %] | Pressure [bar] | ture [°C.] | WHSV 0.7 [g/g · h] | WHSV 1.5 [g/g · h] | WHSV 3 [g/g · h] | liter [kg/l] |
| A | 40 | 280 | 260 | 18.10 | 11.80 | | 0.50 |
| A | 40 | 280 | 270 | 20.02 | 16.53 | 12.12 | 0.50 |
| A | 40 | 280 | 280 | 17.55 | 17.14 | 15.19 | 0.50 |
| A | 40 | 280 | 300 | 12.41 | 12.76 | 12.36 | 0.50 |
| B | 40 | 280 | 270 | 19.12 | 11.50 | 6.16 | 0.63 |
| C | | 280 | 300 | 7.57 | 4.96 | 3.10 | 0.56 |
| D | 40 | 280 | 270 | 12.36 | 8.21 | 5.08 | 0.50 |
| E | 40 | 280 | 270 | 16.50 | 11.40 | 7.52 | 0.67 |
| F | | 280 | 270 | 17.52 | 13.23 | 9.18 | 0.48 |

We claim:

1. A process for preparing amines of the general formula I

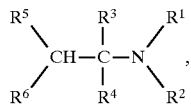 (I)

where

R$^1$, R$^2$, R$^3$, R$^4$, R$^5$ and R$^6$ are each hydrogen, C$_1$–C$_{20}$-alkyl, C$_2$–C$_{20}$-alkenyl, C$_2$–C$_{20}$-alkynyl, C$_3$–C$_{20}$-cycloalkyl, C$_4$–C$_{20}$-alkylcycloalkyl, C$_4$–C$_{20}$-cycloalkylalkyl, aryl, C$_7$–C$_{20}$-alkylaryl or C$_7$–C$_{20}$-aralkyl, R$^1$ and R$^2$ together form a saturated or unsaturated C$_3$–C$_9$-alkylene dichain, or R$^3$ or R$^5$ is C$_{21}$–C$_{200}$-alkyl or C$_{21}$–C$_{200}$-alkenyl or together form a C$_2$–C$_{12}$-alkylene dichain, by reacting olefins of the general formula II

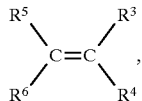 (II)

where R$^3$, R$^4$, R$^5$ and R$^6$ are each as defined above, with ammonia or primary or secondary amines of the general formula III

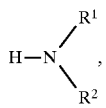 (III)

where R$^1$ and R$^2$ are each as defined above, at temperatures from 200° to 350° C. and pressures from 100° to 300 bar in the presence of a heterogeneous catalyst, which comprises using a heterogeneous catalyst comprising hexagonal faujasite.

2. The process of claim 1, wherein the product amine I is separated off and the unconverted feed materials II and III are recycled.

3. The process of claim 1, wherein olefin II is isobutene, diisobutene, cyclopentene, cyclohexene or polyisobutene.

4. The process of claim 1, wherein the heterogeneous catalyst used comprises dealuminated hexagonal faujasite.

5. The process of claim 1, wherein the hexagonal faujasite heterogeneous catalyst used is in the H-form or in the ammonium form.

6. The process of claim 1, wherein the hexagonal faujasite heterogeneous catalyst used has been treated with an acid.

7. The process of claim 1, wherein the hexagonal faujasite heterogeneous catalyst has been treated with an acid selected from the group consisting of hydrochloric acid, hydrofluoric acid, sulfuric acid, phosphoric acid, oxalic acid and mixtures thereof.

8. The process of claim 1, wherein the hexagonal faujasite heterogeneous catalyst used has been doped with one or more transition metals.

9. The process of claim 1, wherein the hexagonal faujasite heterogeneous catalyst used has been doped with one or more rare earth elements.

10. The process of claim 1, wherein the hexagonal faujasite heterogeneous catalyst used is formed in situ in the reactor by calcination of the template-containing form.

11. The process of claim 1, wherein the hexagonal faujasite heterogeneous catalyst used has been doped with one or more elements from the group of the alkali, alkaline earth or earth metals.

12. The process of claim 1, wherein the hexagonal faujasite heterogeneous catalyst used has been molded with a binder and calcined at from 200° to 600° C.

* * * * *

UNITED STATES PATENT AND TRADEMARK OFFICE
CERTIFICATE OF CORRECTION

PATENT NO.: 5,773,660

DATED: June 30, 1998

INVENTOR(S): ELLER et al.

It is certified that error appears in the above-identified patent and that said Letters Patent is hereby corrected as shown below:

Claim 1, column 7, line 13, after "$C_7$-$C_{20}$-aralkyl," insert --or--.

Claim 1, column 7, line 33, "100°" should be --100--.

Signed and Sealed this

Tenth Day of November 1998

Attest:

BRUCE LEHMAN

Attesting Officer

Commissioner of Patents and Trademarks